US008012082B1

(12) United States Patent
Lefew

(10) Patent No.: US 8,012,082 B1
(45) Date of Patent: Sep. 6, 2011

(54) TELEPHONE-ACTUATED WIRELESS SEXUAL STIMULATING SYSTEM

(76) Inventor: Paul Lefew, Valrico, FL (US)

( * ) Notice: Subject to any disclaimer, the term of this patent is extended or adjusted under 35 U.S.C. 154(b) by 1369 days.

(21) Appl. No.: 11/544,312

(22) Filed: Oct. 7, 2006

(51) Int. Cl.
*A61F 5/00* (2006.01)

(52) U.S. Cl. .......... 600/38

(58) Field of Classification Search .......... 600/38–41; 128/897–898
See application file for complete search history.

(56) References Cited

U.S. PATENT DOCUMENTS 3,978,851 A 9/1976 Sobel
6,368,268 B1 4/2002 Sandvick et al.
6,592,516 B2 7/2003 Lee
7,608,037 B2 * 10/2009 Levy .......... 600/38
* cited by examiner

*Primary Examiner* — John P Lacyk

(57) ABSTRACT

A sexually stimulating system includes a device insertable within a body cavity of a recipient, a signal generated by a non-recipient, and a controller attached to a recipient body. The controller is in wireless communication with the device and includes a mechanism for toggling the device between active and inactive modes based upon instructions from the activation signal. The mechanism generates and transmits a control signal to the device. An internal power supply source and a switch are intermediately seated between the power supply source and the device toggling mechanism. A first communications link transmits the activation signal to the controller and a second communications link transmits the control signal to the device. Each device includes a switch and an internal power supply source electrically mated thereto. A receiver is coupled to a digital to analog converter and a transducer is electrically coupled to the converter.

15 Claims, 9 Drawing Sheets

TELEPHONE-ACTUATED WIRELESS SEXUAL STIMULATING SYSTEM

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to sexual devices and, more particularly, to a telephone actuated wireless sexual stimulating system for pleasing a recipient remotely located from a non-recipient caller.

2. Prior Art

A number of sexual stimulation aids or devices are currently offered that are controlled by a person for self-stimulation, or to stimulate a third party (the "recipient"). Stimulation devices have been developed that allow the operator to control the rate of stimulation, as well as other factors that affect the amount of stimulation imparted to the recipient. These stimulation aids, however, require that the operator directly engage the stimulation aid. Nonetheless, these prior art devices all have the disadvantage that the operator must be in close proximity to the recipient.

One prior art example shows an interactive virtual sexual stimulation system that has one or more user interfaces. Each user interface generally comprises a computer having an input device, video camera, and transmitter. The transmitter is used to interface the computer with one or more sexual stimulation devices, which are also located at the user interface. In accordance with the preferred embodiment, a person at a first user interface controls the stimulation device(s) located at a second user interface. The first and second user interfaces may be connected, for instance, through a web site on the Internet. In another embodiment, a person at a user interface may interact with a prerecorded video feed. The invention is implemented by software that is stored at the computer of the user interface, or at a web site accessed through the Internet. Unfortunately, this example requires the use of two computers. This increases expense to the user as well as limits the areas in which the invention can be used.

Another prior art example shows a self-propelled vehicular unit of a size sufficiently small to be transported across a body surface area to be massaged and includes drive means for propelling the unit while imparting a massaging action to the area traversed and steering elements for steering the unit. A radio control receiver within the unit is responsive to a remotely located transmitter to generate signals which signals are translated through servo mechanism to control the speed and direction of movement of the unit. An element may be attached to the unit to provide a scratching action across the traversed area. The force of either or both the massaging and scratching actions may be varied by altering the weight of the unit. Unfortunately, this prior art example is not small enough to be used in a discreet manner necessary for sexual pleasure outside of a private area.

Accordingly, a need remains for a telephone actuated wireless sexually stimulating system in order to overcome the above-noted shortcomings. The present invention satisfies such a need by providing a system that is simple and easy to use, is lightweight yet durable in design and provides an exciting means of achieving optimal sexual pleasure. Such a system conveniently provides invigorating sexual stimulation on demand and effectively enhances a user sex life. The system advantageously provides a truly erotic experience regardless of the time of day or location. The system is conveniently produced in a variety of models and operational settings to best suit individual needs.

BRIEF SUMMARY OF THE INVENTION

In view of the foregoing background, it is therefore an object of the present invention to provide an apparatus for a telephone actuated wireless sexually stimulating system. These and other objects, features, and advantages of the invention are provided by a telephone actuated wireless sexually stimulating system for pleasing a recipient remotely located from a non-recipient caller.

The system includes a portable sexually stimulating device removably insertable within a cavity of a body of a recipient, an activation signal effectively generated by the non-recipient caller, and a conveniently portable controller removably attached to an exterior portion of the recipient body. Such a portable controller is in wireless communication with the device and advantageously includes a mechanism for automatically toggling the device between active and inactive modes based upon instructions received from the activation signal. Such a device toggling mechanism effectively generates and transmits a control signal to the device.

The device toggling mechanism includes an internal power supply source, and a switch intermediately seated between the power supply source and the device toggling mechanism for effectively interrupting power to the device toggling mechanism when a condition precedent is not satisfied. The device toggling mechanism further includes a first dedicated communications link for wirelessly transmitting the activation signal to the controller and a second dedicated communications link for wirelessly transmitting the control signal to the device. The non-recipient effectively controls an operating mode and an operating duration of the device such that the device is advantageously activated independently of receiving an input from the recipient.

The device toggling mechanism further includes an aerial for effectively amplifying the activation signal and a receiver cooperating with the aerial for decoding the amplified activation signal from the non-recipient. A phone signal verification circuit is electrically coupled to the receiver for authorizing a phone number of the non-recipient caller. Such a phone signal verification circuit effectively generates and transmits a first output signal that has a true value when the phone number of the non-recipient is authorized. A password verification circuit is electrically coupled to the phone signal verification circuit for advantageously verifying an identity of the non-recipient caller. Such a password verification circuit effectively generates and transmits a second output signal that has a true value when the password of the non-recipient is authorized.

The device toggling mechanism further includes an AND gate electrically coupled directly to the phone signal verification circuit and the password verification circuit respectively. Such an AND gate effectively generates and transmits a logic output signal if the first and second output signals have true values. A programming circuit is electrically coupled to the AND gate and is conveniently activated when the logic output signal is received from the AND gate. A timer is electrically coupled to the programming circuit such that the timer advantageously discontinues a programming signal transmitted from the programming circuit after a predetermined time interval has lapsed.

The phone verification circuit includes a processor and a memory electrically coupled to the processor. Such a memory includes programmable software instructions that advantageously verify an identity of the non-recipient caller. Such software instructions include and execute a control logic algorithm including the steps of determining the phone number from which the non-recipient caller is calling, comparing the phone number with a list of accepted phone numbers, and if the phone number is located in the list, then granting permission for the non-recipient caller to continue the phone call, and if the phone number is not located in the list, then canceling the phone call after a predetermined time interval has lapsed.

The password verification circuit includes a processor and a memory electrically coupled to the processor. Such a memory includes programmable software instructions that advantageously verify an identity of the non-recipient caller. Such software instructions include and execute a control logic algorithm including the steps of requesting a numeric password that has a predetermined number of digits, comparing the numeric password with a list of authorized passwords stored in the memory, and if the numeric password is located within the list of authorized passwords, then permitting the non-recipient caller to proceed with the call, and if the numeric password is not located within the list of authorized passwords, then canceling the call after a predetermined time period has lapsed.

The programming circuit includes a processor and a memory electrically coupled to the processor. Such a memory includes programmable software instructions that permit the non-recipient caller to conveniently activate the devices based upon a set of parameters. Such software instructions include and execute a control logic algorithm including the steps of selecting one of the devices to be activated, verifying whether the one device is in an inactive mode, and if the one device is inactive, then choosing at least one of the parameters selected from a group including an activation time, choosing a vibration intensity level, choosing a deactivation time and any combination thereof, and if the one device is active, then notifying the non-recipient caller of the deactivation time and canceling the call after a predetermined time period has lapsed.

Each of such devices includes a manually operable toggle switch and an internal power supply source electrically mated thereto. A receiver for receiving the control signal is electrically coupled to a digital to analog converter such that the converter effectively converts the control signal to an analog signal. A transducer is electrically coupled to the converter and is responsive to the analog control signal for effectively emitting at least one output signal during the predetermined time period. Such an at least one output signal conveniently includes an output signal selected from the group including an audible signal, an illuminated light signal, a vibration signal and any combination thereof respectively.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
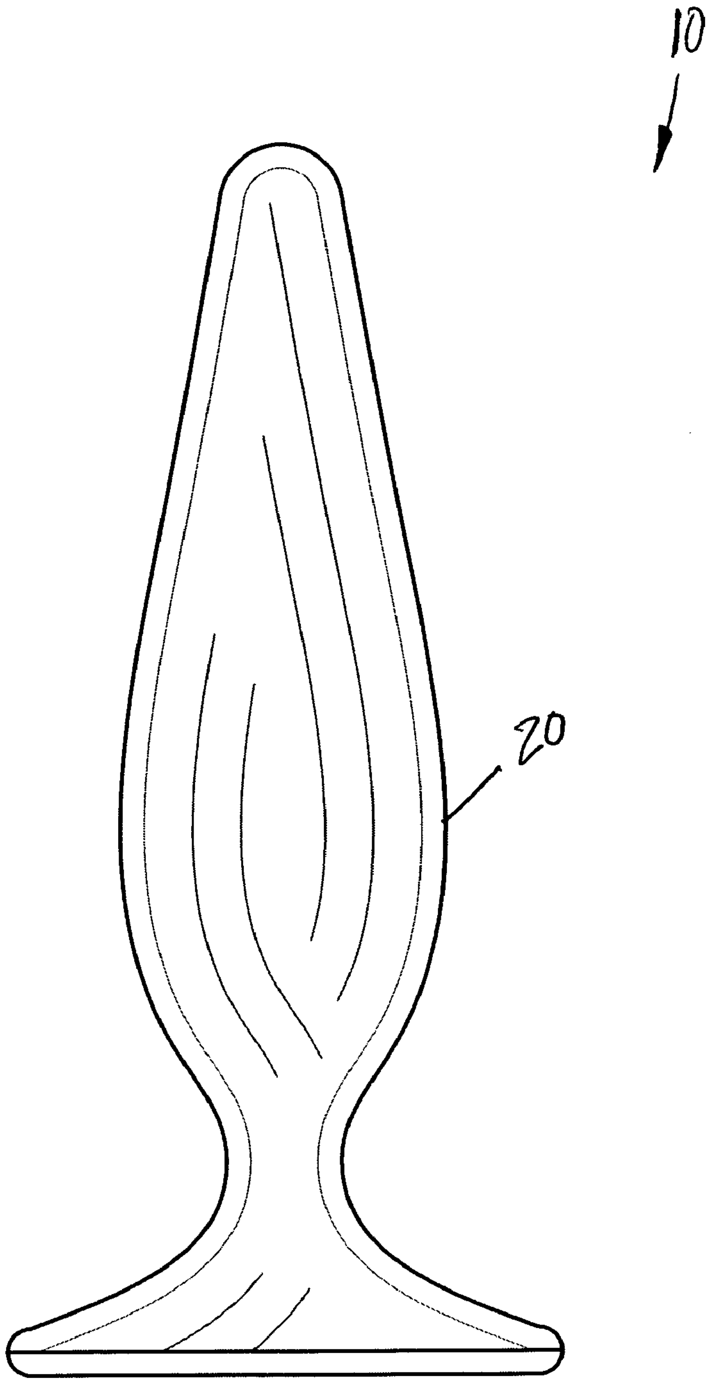
FIG. 1 is a side elevational view showing a portable sexually stimulating device, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The system of this invention is referred to generally in FIGS. 1-7 by the reference numeral 10 and is intended to provide a telephone actuated wireless sexually stimulating system. It should be understood that the system 10 may be used to sexually stimulate many different types of users in many different environments and should not be limited in use to sexually stimulating only those users in those environments described herein.

Figure 2:
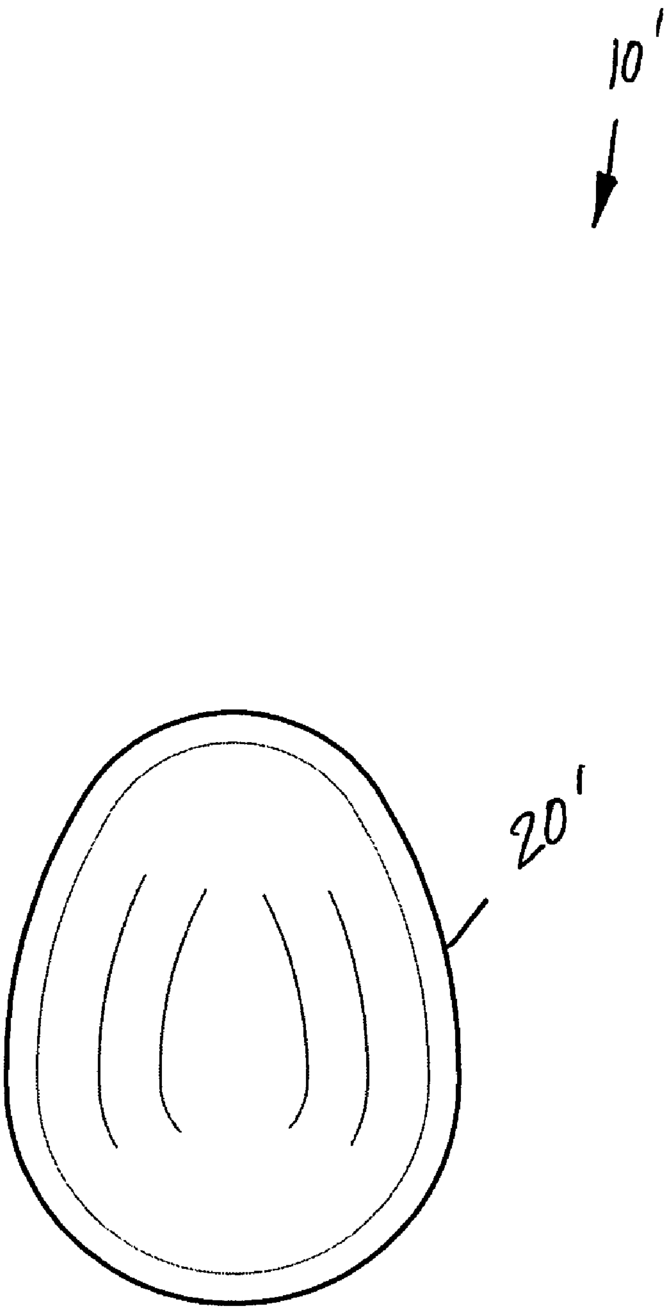
FIG. 2 is a side elevational view showing a portable sexually stimulating device, in an alternate embodiment.
Figure 3:
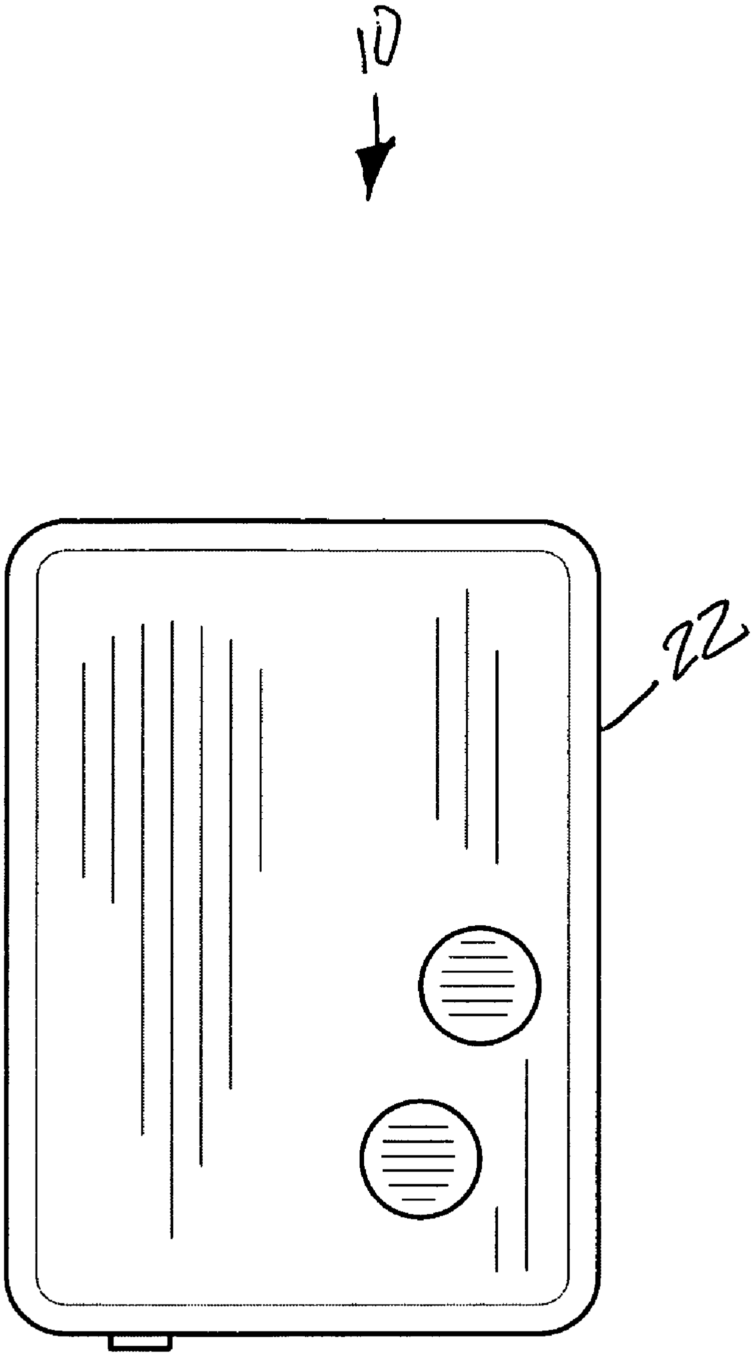
FIG. 3 is a front elevational view of a beeper, in accordance with the present invention.

Referring initially to FIGS. 1 and 2, the system 10 includes a portable sexually stimulating device 20 and 20' removably insertable within a cavity of a body of a recipient, an activation signal generated by the non-recipient caller, and a portable controller 22 removably attached to an exterior portion of the recipient body. Of course, such a device 20 and 20' can be produced in a variety of shapes and sizes, as is obvious to a person of ordinary skill in the art. Such a portable controller 22 is in wireless communication with the device 20 and 20' and advantageously includes a mechanism 23 for automatically toggling the device 20 and 20' between active and inactive modes based upon instructions received from the activation signal. Such a device toggling mechanism 23 generates and transmits a control signal 24 to the device 20 and 20'.

Figure 5:
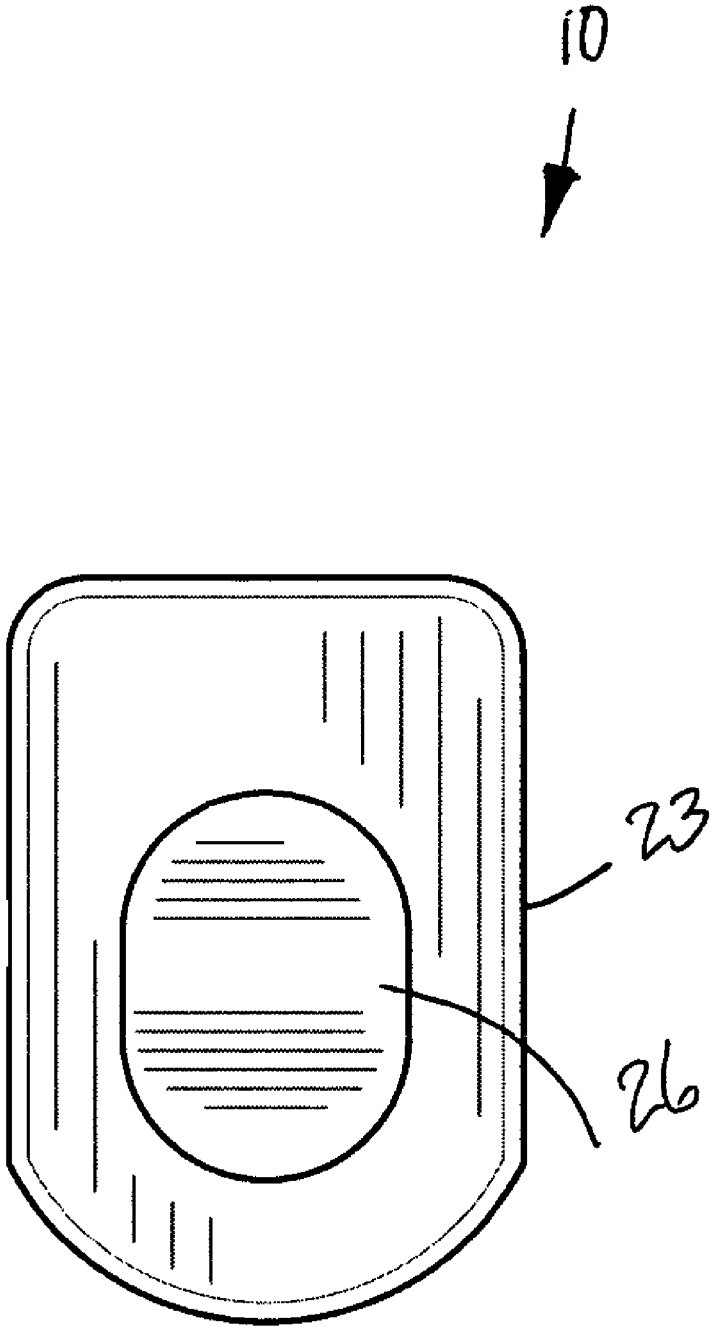
FIG. 5 is a front elevational view of a device toggling mechanism.
Figure 6:
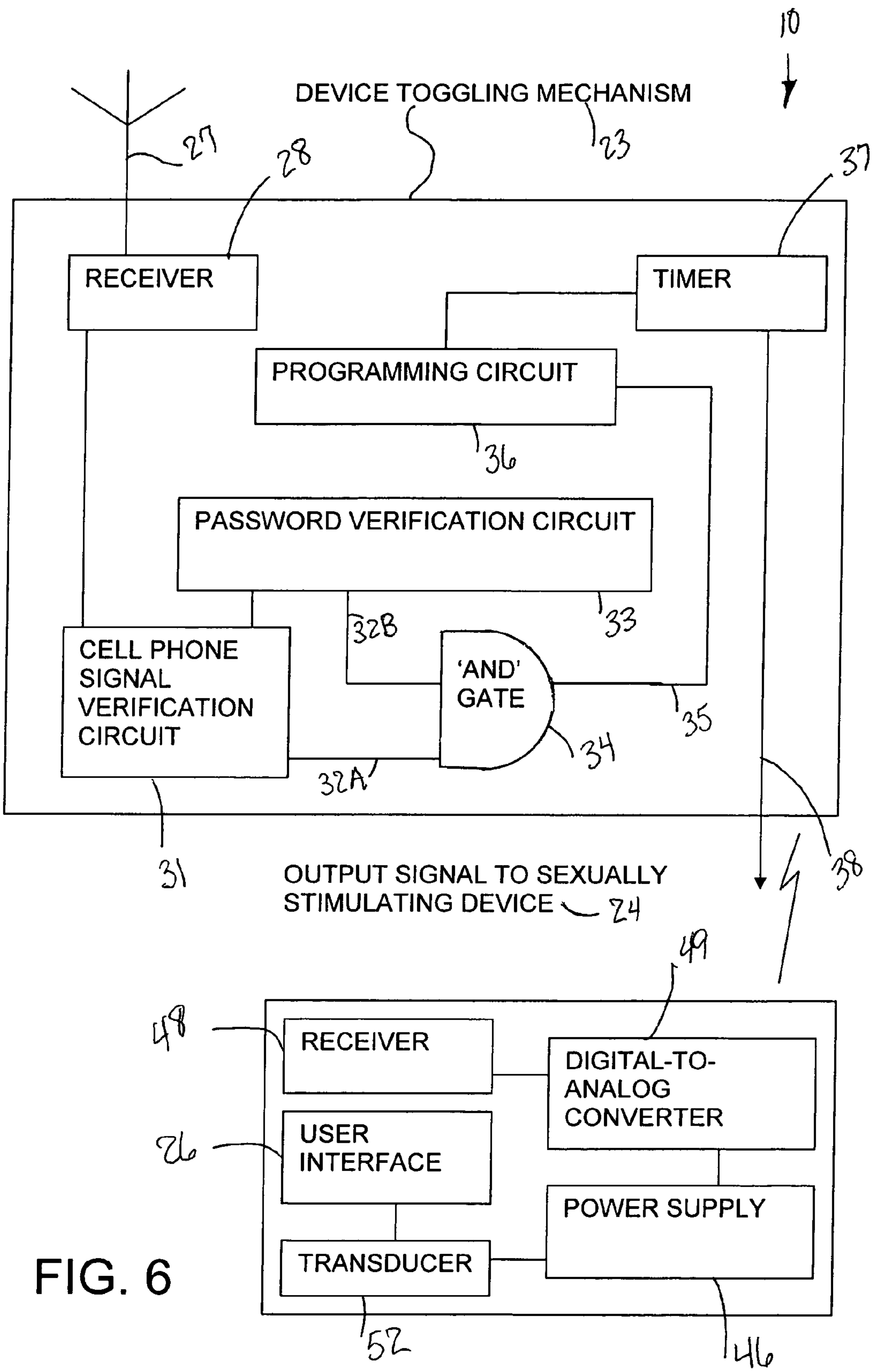
FIG. 6 is a schematic block diagram of a device toggling mechanism.

Referring to FIGS. 5 and 6, the device toggling mechanism 23 includes an internal power supply source 25 and a switch 26 intermediately seated between the power supply source 25 and the device toggling mechanism 23, which is essential for interrupting power to the device toggling mechanism 23 when a condition precedent is not satisfied. The device toggling mechanism 23 further includes a first dedicated communications link, which is crucial for wirelessly transmitting the activation signal to the controller 22 and a second dedicated communications link, which is critical for wirelessly transmitting the control signal 21 to the device 20 and 20'. The non-recipient controls an operating mode and an operating duration of the device 20 and 20', which is vital such that the device 20 and 20' is advantageously activated independently of receiving an input from the recipient.

Referring to FIG. 6, the device toggling mechanism 23 further includes an aerial 27 for amplifying the activation signal 21 and a receiver 28 cooperating with the aerial 27, which is important for decoding the amplified activation signal 29 from the non-recipient. A phone signal verification circuit 31 is electrically coupled to the receiver 28 for authorizing a phone number of the non-recipient caller. Such a phone signal verification circuit 31 generates and transmits a first output signal 32A that has a true value when the phone number of the non-recipient is authorized. A password verification circuit 33 is electrically coupled to the phone signal verification circuit 31, which is essential for advantageously verifying an identity of the non-recipient caller. Such a password verification circuit 33 generates and transmits a second output signal 32B that has a true value when the password of the non-recipient is authorized.

Again referring to FIG. 6, the device toggling mechanism 23 further includes an AND gate 34 electrically coupled directly to the phone signal verification circuit 31 and the password verification circuit 33 respectively, without the use of intervening elements. Such an AND gate 34 generates and transmits a logic output signal 35 if the first and second output signals 32A, 32B have true values. A programming circuit 36 is electrically coupled to the AND gate 34 and is activated when the logic output signal 35 is received from the AND gate 34. A timer 37 is electrically coupled to the programming circuit 36, which is vital such that the timer 37 advantageously discontinues a programming signal 38 transmitted from the programming circuit 36 after a predetermined time interval has lapsed.

Figure 7:
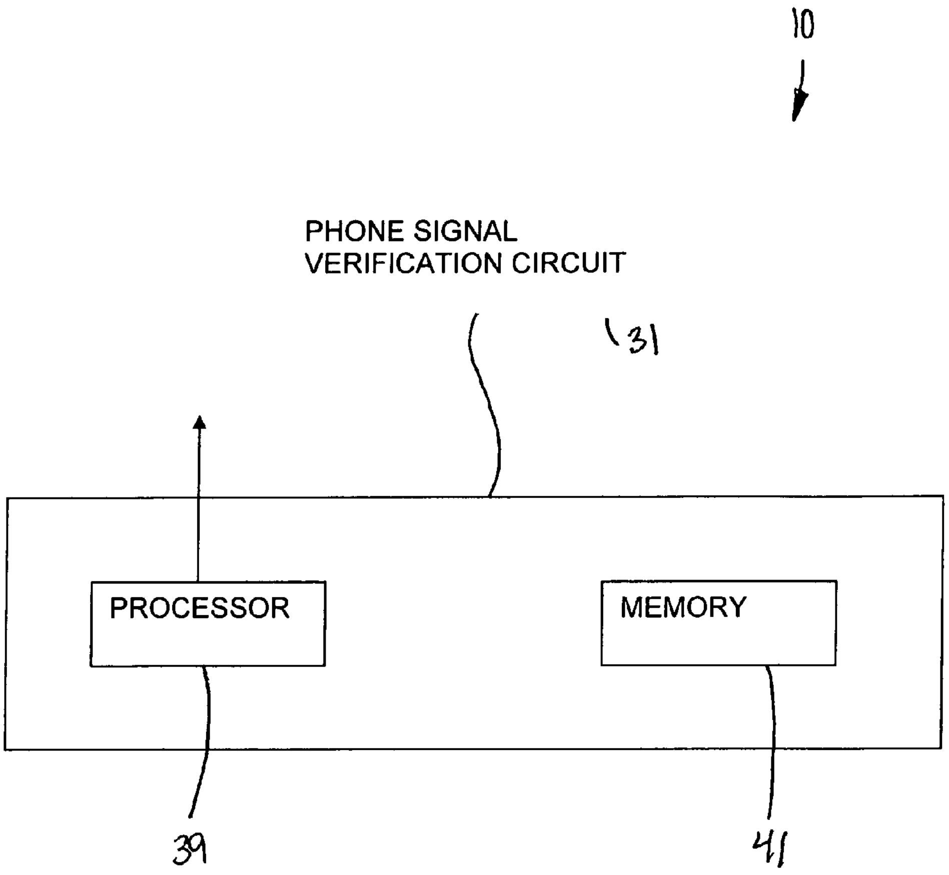
FIG. 7 is a schematic block diagram of a phone signal verification circuit.

Referring to FIGS. 6 and 7, the phone signal verification circuit 31 includes a processor 39 and a memory 41 electrically coupled to the processor 39. Such a memory 41 includes programmable software instructions that advantageously verify an identity of the non-recipient caller. Such software instructions include and execute a control logic algorithm including the steps of determining the phone number from which the non-recipient caller is calling, comparing the phone number with a list of accepted phone numbers, and if the phone number is located in the list, then granting permission for the non-recipient caller to continue the phone call, and if the phone number is not located in the list, then canceling the phone call after a predetermined time interval has lapsed.

Figure 8:
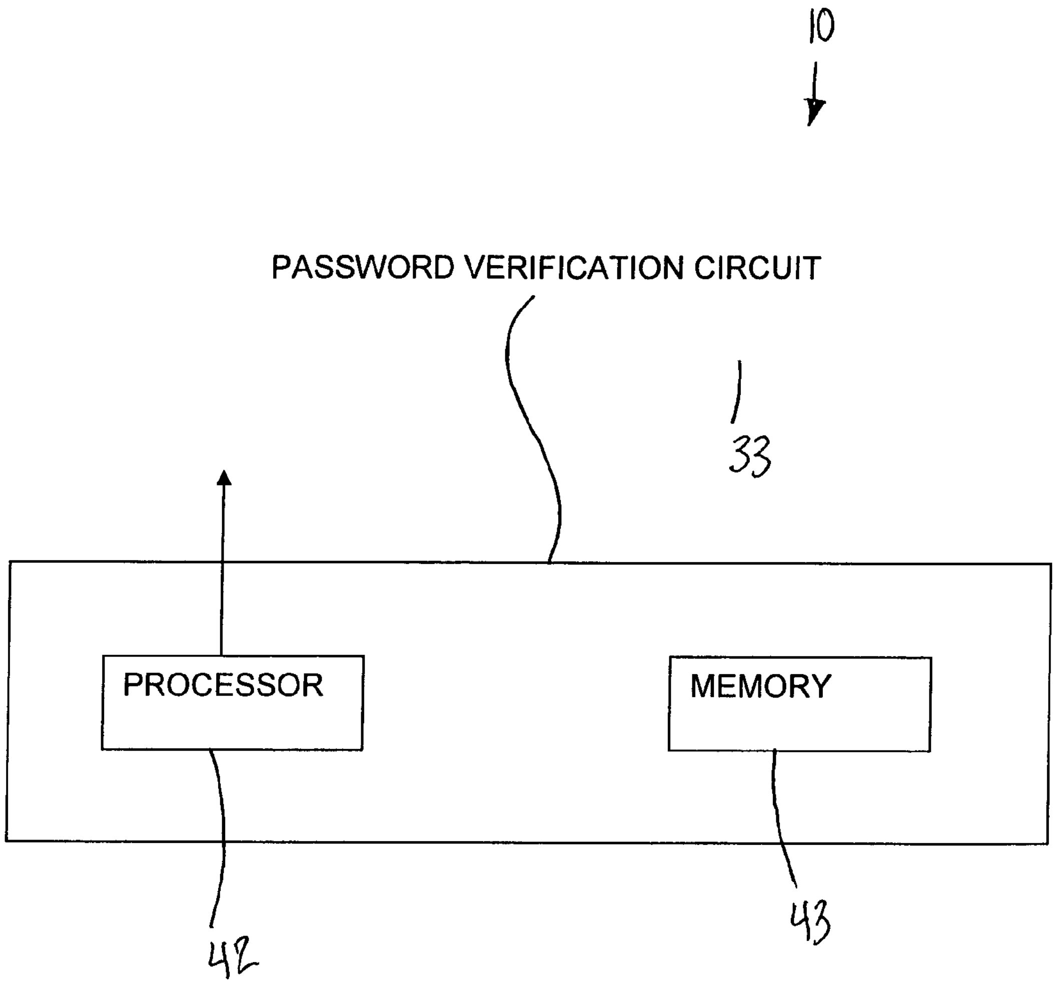
FIG. 8 is schematic block diagram of a password verification circuit.

Referring to FIGS. 6 and 8, the password verification circuit 33 includes a processor 42 and a memory 43 electrically coupled to the processor 42. Such a memory 43 includes programmable software instructions that advantageously verify an identity of the non-recipient caller. Such software instructions include and execute a control logic algorithm including the steps of requesting a numeric password that has a predetermined number of digits, comparing the numeric password with a list of authorized passwords stored in the memory 43, and if the numeric password is located within the list of authorized passwords, then permitting the non-recipient caller to proceed with the call, and if the numeric password is not located within the list of authorized passwords, then canceling the call after a predetermined time period has lapsed.

Figure 9:
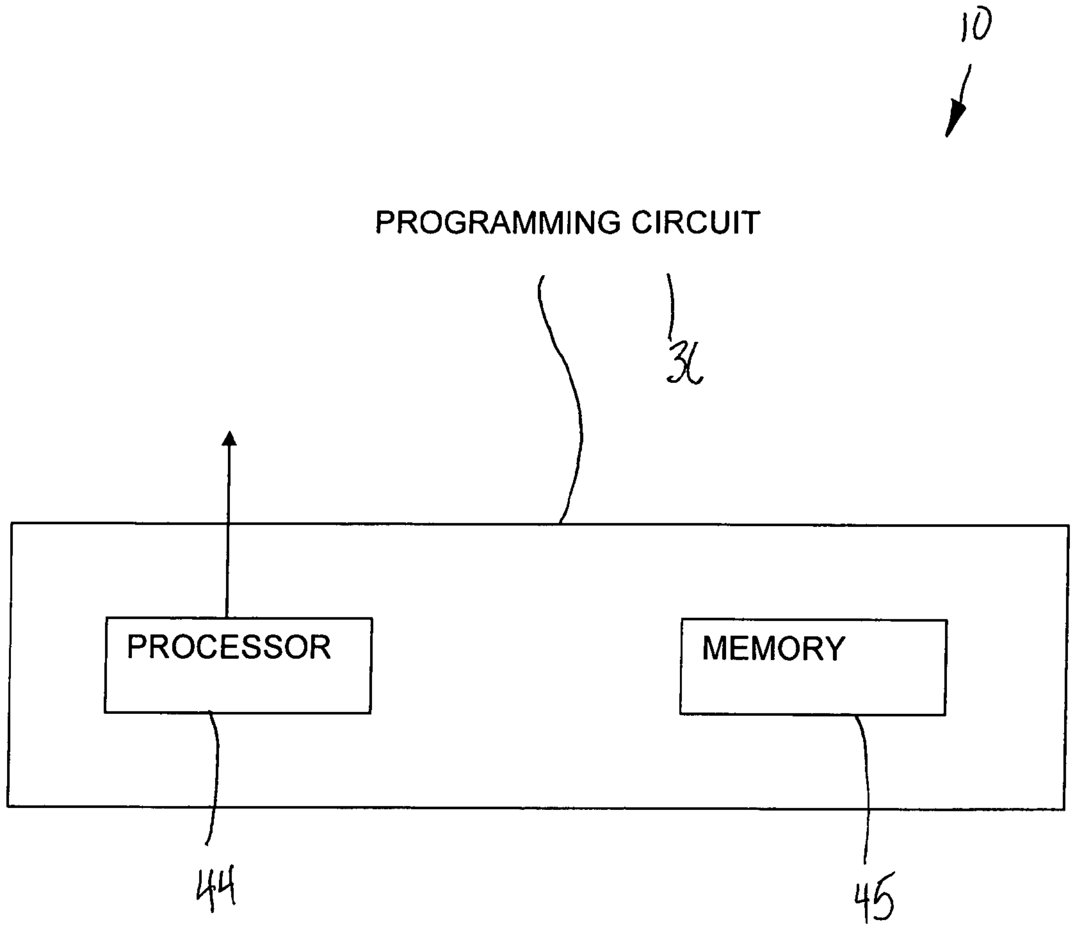
FIG. 9 is a schematic block diagram of a programming circuit.

Referring to FIGS. 6 and 9, the programming circuit 36 includes a processor 44 and a memory 45 electrically coupled to the processor 44. Such a memory 45 includes programmable software instructions that permit the non-recipient caller to conveniently activate the devices 20, 20' and 22 based upon a set of parameters. Such software instructions include and execute a control logic algorithm including the steps of selecting one of the devices 20, 20' and 22 to be activated, verifying whether the one device 20, 20' and 22 is in an inactive mode, and if the one device 20, 20' and 22 is inactive, then choosing at least one of the parameters selected from a group including an activation time, choosing a vibration intensity level, choosing a deactivation time and any combination thereof, and if the one device 20, 20' and 22 is active, then notifying the non-recipient caller of the deactivation time and canceling the call after a predetermined time period has lapsed.

Yet again referring to FIGS. 5 and 6, each of such devices 20, 20' and 22 includes a manually operable toggle switch 26 and an internal power supply source 46 electrically mated thereto. A receiver 47 for receiving the control signal 48 is electrically coupled to a digital to analog converter 49, which is critical such that the converter 49 advantageously converts the control signal to an analog signal. A transducer 52 is electrically coupled to the converter 49 and is responsive to the analog signal, which is crucial for emitting at least one output signal during the predetermined time period. Such an at least one output signal includes an output signal selected from the group including an audible signal, an illuminated light signal, a vibration signal and any combination thereof respectively.

Use of the system 10 is very simple and straight forward. After purchasing the system 10, a user subscribes to a pager service in order to obtain an activation code. The user then applies the device 20, 20' to an area of the body and wears the device 20, 20' to work, school or anywhere else, making sure to store the controller 22 nearby in order to remotely activate the device 20, 20'. The user partner then activates the device 20, 20' from any location, at any time, by dialing the designated number via any telephone and entering the activation code, thus remotely activating the device 20, 20' and providing the user with unexpected and delightful sexual stimulation. The ability to remotely activate the device 20, 20' provides the unexpected benefit of convenience and portability, thereby overcoming prior art shortcomings.

Figure 4:
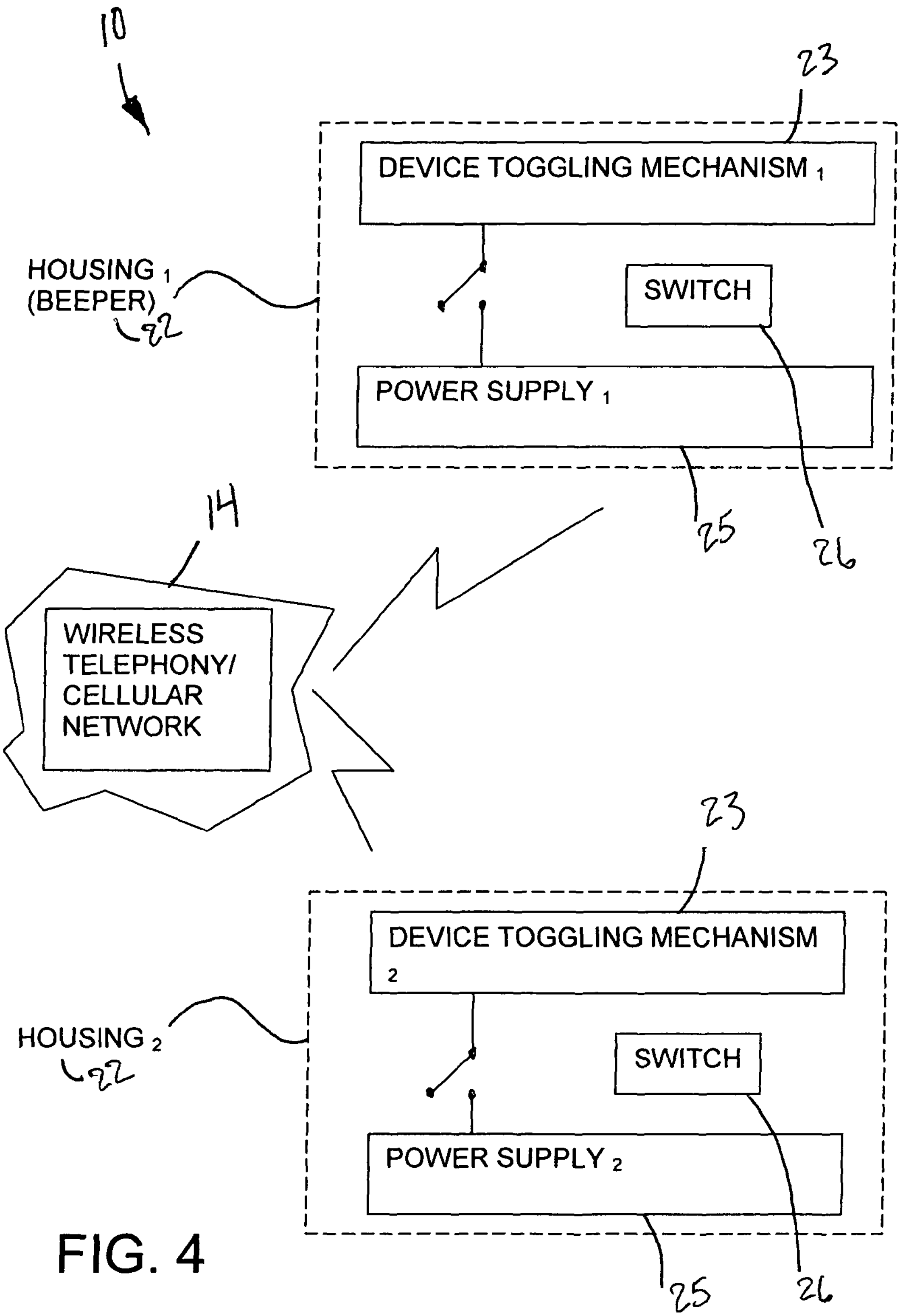
FIG. 4 is a schematic block diagram of a telephone actuated wireless sexually stimulating system.

In operation a device 20, such as a sexually simulating article, contains a triggerable device toggling mechanism 23, as shown in FIG. 4. The device 20 is most likely hidden somewhere within a cavity of a recipient, such as in the rectum or vaginal areas. For example, the device 20 may be strapped to a recipient's waist or genital areas. Additionally, a portable controller 22, such as a beeper or pager, is worn outside of the recipient's clothing and may be housed within a purse or jacket pocket, for example.

Upon instructions for a non-recipient caller, the portable controller 22 receives a page from a paging satellite (not shown) preferably initiated by personnel or some automatic device located at the service provider (such as the telephone company or the like). The page request can be initiated from any source, such as a non-recipient caller's cell phone, LAN phone or a Voice over Internet Protocol having a dial-in interface, for example. The service provider transmits encoded regulating signals for instructing the portable controller to perform a series of operations based upon a user input generated on a cell phone. For example, a non-recipient caller may request that the service provider send a control signal to the portable controller 22 which causes the device to automatically toggle between operating and non-operating modes, at a selected intensity and for a predetermined duration of time, for example. The service provider's response is to send a page to a phone number dedicated to the portable controller, which is positioned on the recipient of the device.

The page need not originate in the paging satellite but can originate in any system capable of sending out pages. For example, a cellular network may be capable of sending out pages and could be used instead of the paging satellite. Further, the system need not use a page to communicate between the service provider and the portable controller 22 but can use any system that allows the service provider to uniquely address the portable controller 22 via a broadcast signal. For example, very low frequency signals or HF radio signals could be used to communicate between the service provider and the portable controller 22.

When the central station receives the page, it determines the portable controller's 22 location and direction of movement by accessing the signals of the GPS system, which comprises a plurality of satellites broadcasting signals which can be used to determine an object's location heading anywhere on the earth, as well known in the industry. The central station then formats the location information into a cellular telemetry stream and transmits it via the cellular system's telemetry channels. Advantageously, a non-recipient caller, for example, can manually activate and deactivate the system via a conventional hand-operable cellular telephone, as described hereinbelow.

In the AMPS (Advanced Mobile Phone System) cellular system, which is the analog cellular system used in the United States, each cellular base station has 832 channels. The 832 channels are divided among at least two competing cellular carriers. Each cellular carrier uses 21 of the 416 channels to carrying control signals. Each control channel includes a Forward Control Channel (FOCC) and a Reverse Control Channel (RECC).

The cellular base station uses the FOCC to send information to cellular telephones and the cellular telephones send information back to the cellular base station via the RECC. The FOCC and RECC are used to establish a cellular telephone call through a local switch. Once the cellular telephone call is established, the call is moved to one of the non-control channels and the released control channel is made available to establish other cellular telephone calls.

The cellular base station broadcasts a System Identification ("SID") signal, which identifies the cellular system to cellular telephones receiving it. When a cellular telephone is turned on, it compares the SID signal it receives against a SID stored within the telephone, which identifies the cellular telephone's home system. If the received SID is not the same as the stored SID, the cellular telephone is "roaming" and the "roam" indicator on the telephone is illuminated.

Subsequently, the cellular telephone transmits its identity to the cellular base station via the RECC. The RECC transmission includes the telephone's Mobile Identification Number ("MIN"), which is a unique 10-digit number (analogous to a telephone number including an area code) that is programmed into the cellular telephone. The first six digits of the MIN identify the cellular telephone's home system. The RECC also includes an Electronic Serial Number ("ESN"), a unique 32-bit serial number permanently stored in the cellular telephone which uniquely identifies the cellular telephone. The cellular base station will receive the MIN and ESN through the RECC and determine that the MIN does not correspond to a local number. Using the MIN, the cellular base station will determine the home system for the cellular telephone and send a validation signal to that system. The cellular local switches in the United States are interconnected through the Intersystem Signaling Network, IS-41, which allows them to send and receive validation information.

The validation signal, known under IS-41 as a Registration/Notification Invoke (REGNOT) message, includes the cellular telephone's MIN and ESN. The REGNOT message also includes the identity of the cellular base station sending the message. The cellular telephone's home system will respond with a Registration/Notification Return Result (REGNOT) message. In the REGNOT message, the cellular telephone's home system will either indicate that it will take financial responsibility for calls made by the cellular telephone or it will refuse to validate the cellular telephone. If validation occurs, a subsequent exchange of messages establishes the features (such as call forwarding) available to the cellular telephone.

The validation process just described uses the cellular system's control channels. Again, once a cellular telephone call is initiated the control channel that was used to set up the call is released for other purposes.

Returning to FIGS. 4 and 6, upon receipt of the page from GPS satellite, the control system (transmitter controller) determines the location and direction of movement, if any, of the recipient using the GPS signals from the GPS system. The system then formats the location and movement information into the payload portion of a cellular RECC signal and transmits it to a local cellular base station 24. The MIN portion of the RECC signal may contain a unique MIN or it may be a MIN that is common to all triggerable location-reporting apparatus serviced by a common service provider. Alternatively, the MIN may be different for each of the apparatus.

The service provider can now communicate the instructions of the non-recipient caller to the portable controller 22 provided that the non-recipient caller's identity can be confirmed and the recipient has not powered their portable controller to an off position.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

The invention claimed is:

1. A telephone actuated wireless sexual stimulating system for pleasing a recipient remotely located from a non-recipient caller, said wireless sexual stimulating system comprising:

a portable sexually stimulating device adapted to be removably inserted within a cavity of a body of a recipient;

an activation signal generated by the non-recipient caller;

a portable controller adapted to be removably attached to an exterior portion of the recipient body, said portable controller being in wireless communication with said device and comprising:

means for automatically toggling said device between active and inactive modes based upon instructions received from said activation signal, said device toggling means generating and transmitting a control signal to said device, an internal power supply source, and a switch intermediately seated between said power supply source and said device toggling means for interrupting power to said device toggling means when a condition precedent is not satisfied;

a first dedicated communications link for wirelessly transmitting said activation signal to said controller; and a second dedicated communications link for wirelessly transmitting said control signal to said device;

wherein said non-recipient controls an operating mode and an operating duration of said device such that said device is activated independently of receiving an input from said recipient.

2. The telephone actuated wireless sexual stimulating system of claim 1, wherein said device toggling means comprises:

an aerial amplifying said activation signal;

a receiver cooperating with said aerial for decoding said amplified activation signal from said non-recipient;

a phone signal verification circuit electrically coupled to said receiver, said phone signal verification circuit authorizing a phone number of the non-recipient caller, said phone signal verification circuit generating and transmitting a first output signal having a true value when the phone number of the non-recipient is authorized;

a password verification circuit electrically coupled to said phone signal verification circuit, said password verification circuit verifying an identity of said non-recipient caller, said password verification circuit generating and transmitting a second output signal having a true value when the password of the non-recipient is authorized;

an AND gate electrically coupled directly to said phone signal verification circuit and said password verification circuit, said AND gate generating and transmitting a logic output signal if said first and second output signals have true values;

a programming circuit electrically coupled to said AND gate, said programming circuit being activated when said logic output signal is received from said AND gate; and a timer electrically coupled to said programming circuit, wherein said timer discontinues a programming signal transmitted from said programming circuit after a predetermined time interval has lapsed.

3. The telephone actuated wireless sexual stimulating system of claim 2, wherein said phone verification circuit comprises:

a processor;

a memory electrically coupled to said processor and including programmable software instructions that verify an identity of the non-recipient caller, said software instruction including and executing a control logic algorithm including the steps of a. determining the phone number from which the non-recipient caller is calling, b. comparing the phone number with a list of accepted phone numbers, c. if the phone number is located in the list, then granting permission for the non-recipient caller to continue the phone call, and d. if the phone number is not located in the list, then canceling the phone call after a predetermined time interval has lapsed.

4. The telephone actuated wireless sexual stimulating system of claim 2, wherein said password verification circuit comprises:

a processor;

a memory electrically coupled to said processor and including programmable software instructions that verify an identity of the non-recipient caller, said software instruction including and executing a control logic algorithm including the steps of a. requesting a numeric password having a predetermined number of digits, b. comparing said numeric password with a list of authorized passwords stored in said memory, c. if said numeric password is located within said list of authorized passwords, then permitting the non-recipient caller to proceed with the call, and d. if said numeric password is not located within said list of authorized passwords, then cancelling the call after a predetermined time period has lapsed.

5. The telephone actuated wireless sexual stimulating system of claim 2, wherein said programming circuit comprises:

a processor;

a memory electrically coupled to said processor and including programmable software instructions that permit the non-recipient caller to activate said devices based upon a set of parameters, said software instruction including and executing a control logic algorithm including the steps of a. selecting one of said devices to be activated, b. verifying whether said one device is in an inactive mode, c. if said one device is inactive, then choosing at least one of said parameters selected from a group including an activation time, choosing a vibration intensity level, choosing a deactivation time and any combination thereof, d. if said one device is active, then notifying the non-recipient caller of said deactivation time and cancelling the call after a predetermined time period has lapsed.

6. A telephone actuated wireless sexually stimulating system for pleasing a recipient remotely located from a non-recipient caller, said wireless sexual stimulating system comprising:

a portable sexually stimulating device adapted to be removably inserted within a cavity of a body of a recipient;

an activation signal generated by the non-recipient caller;

a portable controller adapted to be removably attached to an exterior portion of the recipient body, said portable controller being in wireless communication with said device and comprising:

means for automatically toggling said device between active and inactive modes based upon instructions received from said activation signal, said device toggling means generating and transmitting a control signal to said device, an internal power supply source, and a switch intermediately seated between said power supply source and said device toggling means for interrupting power to said device toggling means when a condition precedent is not satisfied;

a first dedicated communications link for wirelessly transmitting said activation signal to said controller; and a second dedicated communications link for wirelessly transmitting said control signal to said device;

wherein said non-recipient controls an operating mode and an operating duration of said device such that said device is activated independently of receiving an input from said recipient;

wherein said device comprises an internal power supply source electrically mated to said toggle switch;

a receiver for receiving said control signal;

a digital to analog converter electrically coupled to said receiver, said converter converting said control signal to an analog signal; and a transducer electrically coupled to said converter, said transducer being responsive to said analog control signal for emitting at least one output signal during the predetermined time period.

7. The telephone actuated wireless sexual stimulating system of claim 6, wherein said device toggling means comprises:

an aerial amplifying said activation signal;

a receiver cooperating with said aerial for decoding said amplified activation signal from said non-recipient;

a phone signal verification circuit electrically coupled to said receiver, said phone signal verification circuit authorizing a phone number of the non-recipient caller, said phone signal verification circuit generating and transmitting a first output signal having a true value when the phone number of the non-recipient is authorized;

a password verification circuit electrically coupled to said phone signal verification circuit, said password verification circuit verifying an identity of said non-recipient caller, said password verification circuit generating and transmitting a second output signal having a true value when the password of the non-recipient is authorized;

an AND gate electrically coupled directly to said phone signal verification circuit and said password verification circuit, said AND gate generating and transmitting a logic output signal if said first and second output signals have true values;

a programming circuit electrically coupled to said AND gate, said programming circuit being activated when said logic output signal is received from said AND gate; and a timer electrically coupled to said programming circuit, wherein said timer discontinues a programming signal transmitted from said programming circuit after a predetermined time interval has lapsed.

8. The telephone actuated wireless sexual stimulating system of claim 7, wherein said phone verification circuit comprises:

a processor;

a memory electrically coupled to said processor and including programmable software instructions that verify an identity of the non-recipient caller, said software instruction including and executing a control logic algorithm including the steps of a. determining the phone number from which the non-recipient caller is calling, b. comparing the phone number with a list of accepted phone numbers, c. if the phone number is located in the list, then granting permission for the non-recipient caller to continue the phone call, and d. if the phone number is not located in the list, then canceling the phone call after a predetermined time interval has lapsed.

9. The telephone actuated wireless sexual stimulating system of claim 7, wherein said password verification circuit comprises:

a processor;

a memory electrically coupled to said processor and including programmable software instructions that verify an identity of the non-recipient caller, said software instruction including and executing a control logic algorithm including the steps of a. requesting a numeric password having a predetermined number of digits, b. comparing said numeric password with a list of authorized passwords stored in said memory, c. if said numeric password is located within said list of authorized passwords, then permitting the non-recipient caller to proceed with the call, and d. if said numeric password is not located within said list of authorized passwords, then canceling the call after a predetermined time period has lapsed.

10. The telephone actuated wireless sexual stimulating system of claim 7, wherein said programming circuit comprises:

a processor;

a memory electrically coupled to said processor and including programmable software instructions that permit the non-recipient caller to activate said devices based upon a set of parameters, said software instruction including and executing a control logic algorithm including the steps of a. selecting one of said devices to be activated, b. verifying whether said one device is in an inactive mode, c. if said one device is inactive, then choosing at least one of said parameters selected from a group including an activation time, choosing a vibration intensity level, choosing a deactivation time and any combination thereof, if said one device is active, then notifying the non-recipient caller of said deactivation time and canceling the call after a predetermined time period has lapsed.

11. A telephone actuated wireless sexually stimulating system for pleasing a recipient remotely located from a non-recipient caller, said wireless sexual stimulating system comprising:

a portable sexually stimulating device adapted to be removably inserted within a cavity of a body of a recipient;

an activation signal generated by the non-recipient caller;

a portable controller adapted to be removably attached to an exterior portion of the recipient body, said portable controller being in wireless communication with said device and comprising:

means for automatically toggling said device between active and inactive modes based upon instructions received from said activation signal, said device toggling means generating and transmitting a control signal to said device, an internal power supply source, and a switch intermediately seated between said power supply source and said device toggling means for interrupting power to said device toggling means when a condition precedent is not satisfied;

a first dedicated communications link for wirelessly transmitting said activation signal to said controller; and a second dedicated communications link for wirelessly transmitting said control signal to said device;

wherein said non-recipient controls an operating mode and an operating duration of said device such that said device is activated independently of receiving an input from said recipient;

wherein device comprises an internal power supply source electrically mated to said toggle switch;

a receiver for receiving said control signal;

a digital to analog converter electrically coupled to said receiver, said converter converting said control signal to an analog signal; and a transducer electrically coupled to said converter, said transducer being responsive to said analog control signal for emitting at least one output signal during the predetermined time period;

wherein said at least one output signal comprises:

an output signal selected from the group including an audible signal, an illuminated light signal, a vibration signal and any combination thereof respectively.

12. The telephone actuated wireless sexual stimulating system of claim 11, wherein said device toggling means comprises:

an aerial amplifying said activation signal;

a receiver cooperating with said aerial for decoding said amplified activation signal from said non-recipient;

a phone signal verification circuit electrically coupled to said receiver, said phone signal verification circuit authorizing a phone number of the non-recipient caller, said phone signal verification circuit generating and transmitting a first output signal having a true value when the phone number of the non-recipient is authorized;

a password verification circuit electrically coupled to said phone signal verification circuit, said password verification circuit verifying an identity of said non-recipient caller, said password verification circuit generating and transmitting a second output signal having a true value when the password of the non-recipient is authorized;

an AND gate electrically coupled directly to said phone signal verification circuit and said password verification circuit, said AND gate generating and transmitting a logic output signal if said first and second output signals have true values;

a programming circuit electrically coupled to said AND gate, said programming circuit being activated when said logic output signal is received from said AND gate; and a timer electrically coupled to said programming circuit, wherein said timer discontinues a programming signal transmitted from said programming circuit after a predetermined time interval has lapsed.

13. The telephone actuated wireless sexual stimulating system of claim 12, wherein said phone verification circuit comprises:

a processor;

a memory electrically coupled to said processor and including programmable software instructions that verify an identity of the non-recipient caller, said software instruction including and executing a control logic algorithm including the steps of a. determining the phone number from which the non-recipient caller is calling, b. comparing the phone number with a list of accepted phone numbers, c. if the phone number is located in the list, then granting permission for the non-recipient caller to continue the phone call, and d. if the phone number is not located in the list, then canceling the phone call after a predetermined time interval has lapsed.

14. The telephone actuated wireless sexual stimulating system of claim 12, wherein said password verification circuit comprises:

a processor;

a memory electrically coupled to said processor and including programmable software instructions that verify an identity of the non-recipient caller, said software instruction including and executing a control logic algorithm including the steps of a. requesting a numeric password having a predetermined number of digits, b. comparing said numeric password with a list of authorized passwords stored in said memory, c. if said numeric password is located within said list of authorized passwords, then permitting the non-recipient caller to proceed with the call, and d. if said numeric password is not located within said list of authorized passwords, then canceling the call after a predetermined time period has lapsed.

15. The telephone actuated wireless sexual stimulating system of claim 12, wherein said programming circuit comprises:

a processor;

a memory electrically coupled to said processor and including programmable software instructions that permit the non-recipient caller to activate said devices based upon a set of parameters, said software instruction including and executing a control logic algorithm including the steps of a. selecting one of said devices to be activated, b. verifying whether said one device is in an inactive mode, c. if said one device is inactive, then choosing at least one of said parameters selected from a group including an activation time, choosing a vibration intensity level, choosing a deactivation time and any combination thereof, if said one device is active, then notifying the non-recipient caller of said deactivation time and canceling the call after a predetermined time period has lapsed.

* * * * *